United States Patent [19]

Cook et al.

[11] Patent Number: 4,619,996

[45] Date of Patent: Oct. 28, 1986

[54] PROCESS FOR PREPARING 2-β-D-RIBOFURANOSYLSELENAZOLE-4-CARBOXAMIDE

[75] Inventors: P. Dan Cook; Dennis J. McNamara, both of Ann Arbor, Mich.

[73] Assignee: Warner-Lambert Company, Morris Plains, N.J.

[21] Appl. No.: 629,287

[22] Filed: Jul. 9, 1984

[51] Int. Cl.$^4$ ................................................ C07H 1/00
[52] U.S. Cl. .................................... 536/55.3; 536/1.1; 536/18.7; 536/53; 536/55
[58] Field of Search ................. 536/1.1, 18.7, 53, 55.3

[56] References Cited

U.S. PATENT DOCUMENTS 4,161,582  7/1979  Weigele et al. .................... 536/55
4,531,001  7/1985  Robins et al. ..................... 536/55

OTHER PUBLICATIONS

Srivastava et al., "Jour. of Medicinal Chemistry", 1983, vol. 26, pp. 445–448.
Just et al., "Can. Jour. Chem.", vol. 54, 1976, pp. 861–866.

*Primary Examiner*—Johnnie R. Brown
*Attorney, Agent, or Firm*—Jerry F. Janssen

[57] ABSTRACT

A chemical process for preparing 2-β-D-ribofuranosyl-selenazole-4-carboxamide, comprises reacting 2,3,5-tri-O-benzoyl-β-D-ribofuranosyl-1-carbonitrile with gaseous hydrogen selenide in a polar organic solvent.

1 Claim, No Drawings

PROCESS FOR PREPARING 2-β-D-RIBOFURANOSYLSELENAZOLE-4-CARBOXAMIDE

BACKGROUND OF THE INVENTION

The present invention is related to chemical processes. More particularly, it is concerned with an improved chemical process for the preparation of 2-β-D-ribofuranosylselenazole-4-carboxamide.

European patent application No. 0 072 977 to Starks Associates, Inc. discloses a method of preparing 2-β-D-ribofuranosylthiazole-4-carboxamide and its utility as an antiviral/antitumor agent.

Srivastava et al., *J. Med. Chem.*, 26:445–448 (1983), have reported the synthesis of the biologically active selenium analog, 2-β-D-ribofuranosyl-selenazole-b 4-carboxamide, involving a step in which a precursor, 2,3,5-tri-O-benzoyl-β-D-ribofuranosyl-1-carbonitrile is reacted in a pressure vessel with liquified hydrogen selenide in excess, serving both as reagent and solvent. This process involves a number of serious disadvantages, especially when the process is employed to produce large quantities of the desired 2-β-D-ribofuranosylselenazole-4-carboxamide as, for example, on a commercial scale.

First, in either laboratory scale synthesis or when scaled up for commercial production, the use of large quantities of the highly toxic hydrogen selenide presents serious safety hazards. Hydrogen selenide is approximately 200 times as toxic as hydrogen cyanide, and extreme care must be exercised in handling the material.

Second, since the prior art process employs an excess of the liquid form of hydrogen selenide, there are required the additional steps of liquifaction of the hydrogen selenide prior to reaction, and the removal of the excess reagent following reaction. This method adds both complexity and additional safety hazards to the overall process.

Third, the prior art process requires extended reaction periods for the step in which hydrogen selenide is reacted with the starting compound. This often results in anomerization of the desired product to the unwanted alpha-anomer. Separation of the alpha- and beta-amomeric forms of the product introduces additional costly and time-consuming steps.

OBJECTS OF THE INVENTION

It is therefore an object of the present invention to provide an improved process for the preparation of 2-β-D-ribofuranosylselenazole-4-carboxamide which minimizes the amount of hydrogen selenide required per mole of product produced.

It is a further object of the present invention to provide an improved process for the preparation of 2-β-D-ribofuranosylselenazole-4-carboxamide which eliminates the need for the use of liquified hydrogen selenide.

It is another object of this invention to provide an improved process for preparing 2β-D-ribofuranosylselenazole-4-carboxamide which decreases the required reaction time.

It is yet another object of the present invention to provide an improved process for the preparation of 2-β-D-ribofuranosylselenazole-4-carboxamide which produces substantially the desired beta-anomer.

These and other and further objects and advantages are achieved in accordance with the present invention wherein an improved process for preparing 2-β-D-ribofuranosylselenazole-4-carboxamide comprises the steps of (a) reacting 2,3,5-tri-O-benzoyl-β-D-ribofuranosyl-1-carbonitrile with gaseous hydrogen selenide in a 1:1 to 1:1.5 molar ratio at a temperature and for a period sufficient to effect substantially complete conversion of said 2,3,5-tri-O-benzoyl-β-D-ribofuranosyl-1-carbonitrile to 2,5-anhydro-3,4,6-tri-O-benzoyl-β-D-allonselenocarboxamide; (b) reacting said 2,5-anhydro-3,4,6-tri-O-benzoyl-β-D-allonselenocarboxamide with ethyl bromopyruvate to produce ethyl 2-(2,3,5-tri-O-benzoyl-β-D-ribofuranosyl)selenazole-4-carboxylate; and (c) thereafter converting said ethyl 2-(2,3,5-tri-O-benzoyl-β-D-ribofuranosyl)selenazole-4-carboxylate to 2-β-D-ribofuranosylselenazole-4-carboxamide.

DETAILED DESCRIPTION

The process of the present invention is depicted in the following Reaction Scheme.

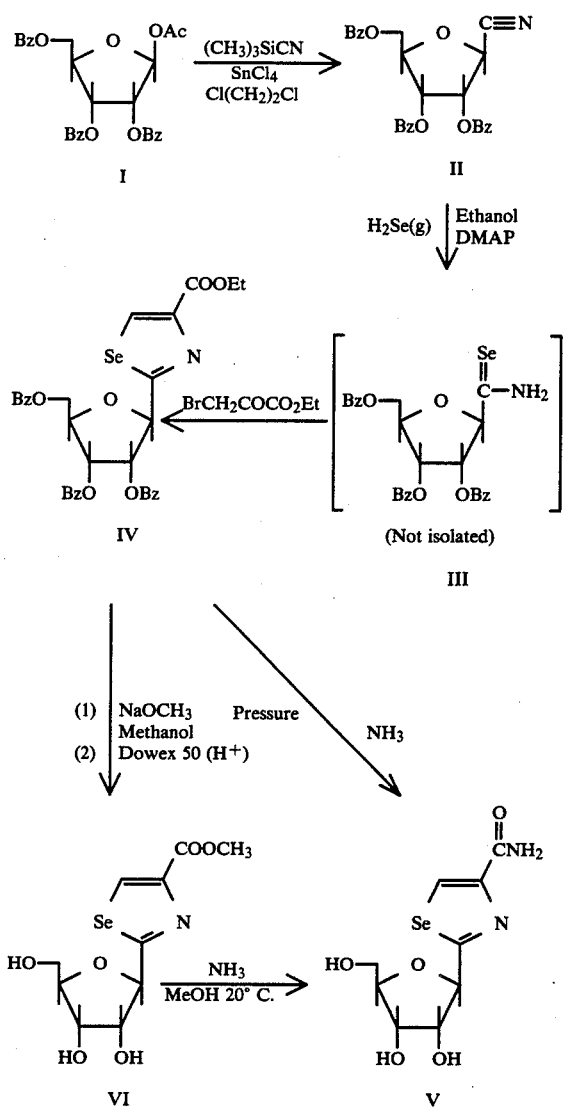

In accordance with the process of the present invention, 2,3,5-tri-O-benzoyl-β-D-βribofuranosyl-1-carbonitrile, (II), is reacted with gaseous hydrogen selenide at atmospheric pressure in a polar solvent employing a basic nitrogen-containing catalyst such as, for example, 4- dimethylaminopyridine. Preferred solvents include the anhydrous lower alcohols such as methanol, ethanol, 1- or 2-propanol and the like, with absolute ethanol being most preferred. Care should be taken to ensure that the solvent is water-free.

A stream of gaseous hydrogen selenide is slowly passed into the solution employing a means for dispersing the gas in the solution such as, for example, a tube outfitted with a porous frit. The outlet gases from the reaction vessel are passed through a trap to capture any escaping hydrogen selenide gas. One simple expedient is the use of a cold water trap. Any hydrogen selenide thus obtained in the cold water trap is converted to its sodium salt with sodium hydroxide solution and is discarded. (Hydrogen selenide is soluble in water to the extent of 3.77 g/ml at 4° C.) Generally, it is found that little, if any, hydrogen selenide escapes from the reaction mixture during the reaction, and the need for a trap is precautionary only.

The 2,3,5-tri-O-benzoyl-$\beta$-D-ribofuranosyl-1-carbonitrile starting material is prepared by the method detailed by M. Bokek and J. Farkas, *Collect. Czech. Chem. Commun.*, 34:247 (1969). Alternatively, it has been found that the compound is produced cleanly in high yield by reaction of the commercially available 1O-acetyl-2,3,5-O-benzoyl-$\beta$-D-ribofuranose, (I), with cyanotrimethylsilane in 1,2-dichloroethane, as detailed in Example 1, below.

As illustrated in Example 2, the gaseous hydrogen selenide is passed into the solution of the carbonitrile until thin-layer chromatographic analysis indicates the substantially complete consumption of the starting material. This usually requires from about 1.0 to 1.5 molar equivalents of gaseous hydrogen selenide per mole of carbonitrile. It is preferred that the amount of hydrogen selenide used be in equimolar ratio to the amount of 2,3,5-O-benzoyl-$\beta$-D-ribofuranosyl-1-carbonitrile. The amount of hydrogen selenide added to the reaction mixture is measured by monitoring the weight gain of the reaction vessel and its contents.

Hydrogen selenide dissolves readily in the solvent employed, and excess hydrogen selenide tends to remain in the reaction solution and undergo a reduction-oxidation reaction with ethyl bromopyruvate in the next step of the process, producing a precipitate of finely divided selenium metal. If a slight excess of hydrogen selenide is used to ensure completeness of reaction, the amount of ethyl bromopyruvate used in the next step of the process is adjusted accordingly to react completely with both the 2,5-anhydro-3,4-6-tri-O-benzoyl-$\beta$-D-allonselenocarboxamide and any excess hydrogen selenide remaining in the solution.

In an alternative embodiment, considerable reduction in the volume of the reaction mixture may be realized with no apparent disadvantage by passing a stream of gaseous hydrogen selenide through a suspension, rather than a solution, of 2,3,5-tri-O-benzoyl-$\beta$-D-ribofuranosyl-1-carbonitrile in the desired solvent. The starting carbonitrile goes into solution as it is converted to the 2,5-anhydro,3,4,6-tri-O-benzoyl-D-allonselenocarboxamide intermediate.

The mixture of carbonitrile and hydrogen selenide should be maintained at a temperature of between about 10° C. and 30° C. during the reaction. The reaction is slightly exothermic, and at temperatures of about 35° C. and above, there is increasing production of an undesirable side-product, probably the alpha-anomeric product. At temperatures below about 10° C., the rate of reaction with the hydrogen selenide is slow, and crystallization of the product interferes with the course of the reaction. The most preferred temperature range for carrying out this step of the reaction is between about 20° C. and 25° C.

When analysis of the reaction mixture indicates the substantially complete consumption of the 2,3,5-tri-O-benzoyl-$\beta$-D-ribofuranosyl-1-carbonitrile, usually after from about one-half to about one and one-half hours, addition of hydrogen selenide is stopped and the 2,5-anhydro-3,4-6-tri-O-benzoyl-$\beta$-D-allonselenocarboxamide, (III), is immediately employed in the next step of the reaction without isolation from the solution, as illustrated by Example 3. The intermediate 2,5-anhydro-3,4-6-tri-O-benzoyl-$\beta$-D-allonselenocarboxamide is unstable, and undergoes both decomposition to the starting materials and anomerization to the undesired alpha-anomer if warmed or allowed to stand for extended periods.

2,5-Anhydro-3,4-6-tri-O-benzoyl-$\beta$-D-allonselenocarboxamide is reacted with ethyl bromopyruvate to produce ethyl 2-(2,3,5-tri-O-benzoyl-$\beta$-D-ribofuranosyl)selenazole-4-carboxylate. As discussed above, if an excess of hydrogen selenide is used in the prior step, excess ethyl bromopyruvate is employed to react with any excess hydrogen selenide.

The ethyl 2-(2,3,5-tri-O-benzoyl-$\beta$-D-ribofuranosyl)-selenazole-4-carboxylate, (IV), resulting from the reaction of the allonselenocarboxamide, (III), with ethyl bromopyruvate is next converted to 2-$\beta$-ribofuranosyl)-selenazole-4-carboxamide, (V), by removing the benzoyl blocking groups and converting the ethyl ester group to a carboxamide. This is achieved by ammonolysis in a pressure vessel at about 100° C. as illustrated by Example 5.

In a preferred alternative method illustrated in Example 6, the ethyl 2-(2,3,5-tri-O-benzoyl-$\beta$-D-ribofuranosyl)selenazole-4-carboxylate, (IV), is treated at atmospheric pressure with sodium methoxide in methanol to remove the benzoyl blocking groups and to convert the ethyl ester to methyl 2-$\beta$-D-ribofuranosyl)-selenazole-4-carboxylate, (VI). This compound is believed to be novel and serves as an easily crystallized intermediate in the production of 2-$\beta$-D-ribofuranosyl-selenazole-4-carboxamide. The methyl 2-($\beta$-D-ribofuranosyl)selenazole-4-carboxylate, VI, is subsequently converted to the desired 2-$\beta$-D-ribofuranosyl-selenazole-4-carboxamide, V, by ammonolysis at atmospheric pressure and at a temperature of about 20° C. in ammonia-saturated methanol.

The procedure of converting the benzoyl-blocked ethyl ester, (IV), to the unblocked methyl ester, (VI) and then to 2-$\beta$-D-ribofuranosylselenazole-4-carboxamide has the advantage of permitting the purification of the easily crystallized methyl ester nucleoside prior to ammonolysis to the desired end product. The direct, single-step ammonolysis at higher temperatures and under pressure tends to lead to the formation of undesired alpha-anomeric product and other unidentified side products which must be subsequently removed in additional steps.

The following examples are provided to enable one skilled in the art to practice the present invention. The examples are merely illustrative, and are not to be read as limiting the scope of the invention as defined by the appended claims.

EXAMPLE 1

(2,3,5-Tri-O-benzoyl-β-D-ribofuranosyl) cyanide (II)

A stirred solution of 1-O-acetyl-2,3,5-tri-O-benzoyl-β-D-ribofuranose (50.3 g, 80 mmol), 1,2-dichloroethane (100 ml), and cyanotrimethylsilane (15.84 g, 160 mmol) was treated in one portion via a syringe with anhydrous stannic chloride (20.8 g, 9.33 ml, 80 mmol). The darkening solution was stirred for two minutes then poured into saturated sodium hydrogen carbonate (800 ml), and stirred five minutes (pH 7). Chloroform (1 liter) was added and the emulsion was filtered through Celite ®. The chloroform layer was separated, dried (MgSO$_4$) and evaporated under reduced pressure (15 torr, 40°) to a light orange syrup which was crystallized from ethanol (charcoal to afford 2 (30 g from two crops, 80%) as long white needles; mp 77°–78° after drying at 0.05 torr, 60° for two hours; $[\alpha]_D^{25}$ +24.4° (0.5 CHCl$_3$).

Anal. Calcd for $C_{27}H_{21}NO_7$ (471.45): C, 68.78; H, 4.49; N, 2.97. Found: C, 68.77; H, 4.45; N, 2.88.

EXAMPLE 2

Ethyl 2-(2,3,5-Tri-O-benzoyl-β-D-ribofuranosyl)selenazole-4-carboxamide (IV)

A mixture of 2,3,5-tri-O-benzoyl-β-D-ribofuranosyl cyanide (II, 612 g, 1.30 mol) 4-dimethylaminopyridine (12 g, 98 mmol) and absolute ethanol (10.0 l) was warmed to 45° with stirring to obtain a complete solution. Argon was dispersed through the solution as it was cooled with a water bath to 20°. The cooling bath was removed and the resulting suspension was treated with gaseous hydrogen selenide (approximately 30 minutes, 108 g, 1.33 mol) via the argon dispersion tube. During the hydrogen selenide treatment, cyanide sugar, II, gradually dissolved and the reaction exotherms to 23°. TLC (SiO$_2$ plates, chloroform-ethyl acetate, 10:1) of the greenish-yellow solution indicates a complete and clean conversion of cyanide sugar to the selenocarboxamide sugar, III. The H$_2$Se flow was replaced with argon and the solution was immediately treated with ethyl bromopyruvate (293 g of 90% purity, 1.33 mol). This mixture was stirred for 0.5 hour and filtered through a bed of Celite ®. The cake was washed with ethanol and then chloroform. The yellow filtrate was adjusted to pH 7-8 by the addition of saturated sodium hydrogen carbonate (1.5 l) and evaporated under reduced pressure to a thick red syrup (15 torr, 50°–60°) which was dissolved in chloroform (2 l) and washed with water (1 l), saturated sodium hydrogen carbonate (1 l), water (1 l), and dried with magnesium sulfate. Evaporation of the dried chloroform solution (15 torr, 60°–70°) provided 826 g (98%) of the blocked selenazole nucleoside, IV, as a thick red syrup (75.1% HPLC).

A portion of the dried syrup (12.8 g, similarly prepared as Example 2) was dissolved in a minimum amount of toluene-ethyl acetate (10:1) and placed on a column of silica gel (200 g packed in toluene-ethyl acetate, 10:1). Elution (4 ml/minute) with toluene-ethyl acetate (10:1) provided the TLC pure (SiO$_2$ plates, chloroform-ethyl acetate, 10:1) product in 750 ml of eluent following 750 ml of forerun. The fractions containing pure material were evaporated under reduced pressure (15 torr, 60°) to afford 10.1 g (79%) of light yellow syrup. A sample was dried at 0.05 torr and 100° for one hour to provided a hard, light yellow foam, $[\alpha]_D^{25}$ −34.7° (1.07% MeOH); $\alpha_{max}$ (MeOH) 229 nm (ε39,917), 259 (7322); pmr (DMSO-d$_6$) δ 8.85 (s, 1, C$_5$H).

Anal. Calcd for $C_{32}H_{27}NO_9Se$ (648.51): C, 59.26; H, 4.20; N, 2.16. Found: C, 59.44; H, 4.21; N, 1.89.

EXAMPLE 3

2-β-D-Ribofuranosylselenazole-4-carboxamide (V)

A solution of red syrup from previous reaction, IV, (93 g, 79% purity, 114 mmol) and methanol (250 ml) was saturated at 0° with ammonia and then heated in a Parr pressure vessel at 95° (steam bath) for six hours (Note 12). The bomb was cooled, vented and the solution evaporated under reduced pressure (15–20 torr, 60°). The residue was coevaporated two times with methanol and the dark brown syrup was dissolved in hot water (50°, 150 ml) and extracted with ethyl acetate (3 ×100 ml). The aqueous layer was treated with charcoal (Darco, MCB, 10 g) and filtered through a bed of Celite ®. The light yellow filtrate was evaporated under reduced pressure (15–20 torr, 60°) to provide a light yellow foam (29 g, 83%) which was dissolved in methanol (50°, 200 ml), absorbed on silica gel (50 g, Kiesel gel 60, 70–230 mesh, EM), and placed on a column of silica gel (250 g packed in chloroform, 7 ×15 cm). Rapid elution (10 ml/minute) with chloroform-methanol (4:1) provided the majority of the crude product in two liters of eluent which was evaporated under reduced pressure (15 torr, 60°). The resulting light yellow residue (30 g) was crystallized from isopropanol (charcoal) to afforded 25.0 g (71%) of 2-β-D-ribofuranosylselenazole-4-carboxamide, V, as faint yellow crystals, mp 130–131°; $[\alpha]_D^{25}$ −20.8° (1.01%.in H$_2$O ); pmr (DMSO-d$_6$): 8.75 (s, 1, C$_5$H), 7.58 (bs, 2, CONH), (DMSO-d$_6$-D$_2$O), 4.88 δ (d, 1, H$_1$, J=5.0 Hz), $\lambda_{max}$ (95% EtOH) 259 nm (ε 6263).

Anal. Calcd for $C_9H_{12}N_2O_5Se$ (307.19): C, 35.19; H, 3.94; N, 9.12. Found: C, 35.38; H, 3.94; N, 9.12.

EXAMPLE 4

Methyl 2-β-D-ribofuranosylselenazole-4-carboxylate (VI)

A gummy suspension of 206.3 g (75.1% pure by HPLC; 0.239 mol) of the blocked ethyl ester, IV, in 700 ml of methanol was heated and stirred on the steam bath until solution occurred. The solution was allowed to cool to room temperature during which time a finely dispersed oily suspension formed. To this suspension was added 17.2 g (318 mmol) of sodium methoxide. The addition was slightly exothermic and resulted in a brown solution. The solution was stirred at room temperature overnight. TLC (SiO$_2$, toluene-ethyl acetate, 10:1) indicated that no starting material remained. To the reaction solution was added 100 g of Dowex 50 W×4 resin (H+) (washed with methanol) and the suspension was stirred for one hour. The resin was filtered off, washed well with methanol, and discarded. The filtrate and washings were evaporated under reduced pressure to give a two phase mixture. The upper, more liquid phase (mainly methyl benzoate) was decanted. The remaining brown viscous gum was triturated two times with ether. (The methyl benzoate was combined with the ether triturates and upon standing yielded some desired product as a solid). The brown viscous gum was treated with approximately 1 l of warm ethanol and triturated. A dark brown material was filtered from the suspension. TLC (SiO$_2$; dichloromethane-methanol, 10:1) indicated that the dark brown material was mostly slower moving impurities in the filtrate and was discarded.

To the ethanol solution of the product was added 250 g of flash silica gel (230–400 mesh) and the ethanol was removed under reduced pressure to give a solid.

The above reaction was done three other times with 185.1 g, 246.0 g, and 189.0 g of ethyl 2-(2,3,5-tri-O-benzoyl-β-D-ribofuranosyl)selenazole-4-carboxylate (75% purity) as the starting material. The only difference between these four reactions was the amount of sodium methoxide required to maintain the molar ratio above.

The four crude reaction products adsorbed onto silica gel were placed on a column of 2600 g of flash silica gel (230–400 mesh) packed with dichloromethane. The column was eluted with dichloromethane containing gradually increasing amounts of methanol (first dichloromethane-methanol, 50:1, then 40:1, 30:1, 20:1, 10:1, 5:1, and finally 2:1). The appropriate fractions were combined and concentrated to give 262 g (85%) of product as a solid. Recrystallization from ethyl acetate gave 168 g (54.5%) of the product TLC (SiO$_2$, dichloromethane-methanol, 10:1) showed this material to be homogenous, R$_f$=0.3.

A small sample of this material was dried at 23°, 0.5 torr for 18 hours to give an analytical sample, mp 114°–116°.

Anal Calcd for C$_{10}$H$_{13}$NO$_6$Se (322.17): C, 37.28; H, 4.07; N, 4.35. Found: C, 37.23; H, 4.06; N, 4.23.

The NMR and IR of this material were consistent with the assigned structure. Also the mass spectrum of this compound (not this specific lot) was consistent with the assigned structure.

2-β-D-Ribofuranosylselenazole-4-carboxamide (V)

A solution of 168 g (521 mmol) of the methyl ester, VI, in 2.0 l of methanol was cooled to approximately 10° and treated with anhydrous ammonia gas for eight hours. The solution was allowed to stand at room temperature overnight. The TLC (SiO$_2$, dichloromethane-methanol, 5:1) indicated complete conversion to the desired product. A very small amount of a red solid was removed by filtration. The filtrate was evaporated under reduced pressure and the residue was recrystallized from 2-propanol and dried at 40° under 0.5 atmospheres to give 136 g (84.9%) of the product, mp 128–130 (lit. (see below) mp 131°–133°).

TLC (SiO$_2$, dichloromethane-methanol, 4:1) showed this material to be homogenous, R$_f$=0.2. The NMR of this material was consistent with the assigned structure and matched that in the literature (P. C. Srivastava and R. K. Robins, *J. Med. Chem.*, 26, 445 (1983)).

Anal. Calcd for C$_9$H$_{12}$N$_2$O$_5$Se (307.2): C, 35.19; H, 3.94; N, 9.12; Se, 25.71. Found: C, 35.07; H, 3.94; N, 9.04; Se, 25.84.

While there have been shown and described what are believed at present to constitute the preferred embodiments, it will be clear to one skilled in the art that various changes and modifications may be made therein without departing from the scope of the invention as defined by the appended claims.

We claim:

1. A process for preparing 2-β-D-ribofuranosylselenazole-4-carboxamide comprising the steps of:
    (a) reacting 2,3,5-tri-O-benzoyl-β-D-ribofuranosyl-1-carbonitrile with gaseous hydrogen selenide in a 1:1 to 1:5 molar ratio at a temperature of between about 10° C. to about 30° C. for a period of less than three hours to effect substantially complete conversion of said 2,3,5-tri-O-benzoyl-β-D-ribofuranosyl-1-carbonitrile to 2,5-anhydro-3,4,6-tri-O-benzoyl-β-D-allonselenocarboxamide;
    (b) reacting said 2,5-anhydro-3,4,6-tri-O-benzoyl-β-D-allonselenocarboxamide with ethyl bromopyruvate to produce ethyl 2-(2,3,5-tri-O-benzoyl-β-D-ribofuranosyl)selenazole-4-carboxylate;
    (c) reacting said ethyl 2-(2,3,5-tri-O-benzoyl-β-D-ribofuranosyl)selenazole-4-carboxylate with sodium methoxide to produce methyl 2-β-D-ribofuranosylselenazole-4-carboxylate; and
    (d) thereafter reacting said methyl 2-β-D-ribofuranosynselenazole-4-carboxylate with ammonia to product 2-β-D-ribofuranosylselenazole-4-carboxamide.

* * * * *